United States Patent
Mayenberger et al.

(10) Patent No.: US 6,261,303 B1
(45) Date of Patent: Jul. 17, 2001

(54) SURGICAL CLIP

(75) Inventors: Rupert Mayenberger, Rielasingen; Dieter Weisshaupt, Immendingen, both of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/458,290

(22) Filed: Dec. 10, 1999

(30) Foreign Application Priority Data

Dec. 18, 1998 (DE) .............................. 198 58 581

(51) Int. Cl.$^7$ .................................................. A61B 17/04
(52) U.S. Cl. .............................................................. 606/151
(58) Field of Search ....................... 606/151–158, 606/138–144; D11/200; D28/39; 267/53; 29/243.56

(56) References Cited

U.S. PATENT DOCUMENTS

| | | | |
|---|---|---|---|
| 2,988,314 | * 6/1961 | Urich | ................................ 606/151 |
| 3,317,973 | 5/1967 | Finkle . | |
| 3,616,497 | 11/1971 | Esposito . | |
| 3,629,912 | 12/1971 | Klopp . | |
| 3,916,908 | 11/1975 | Leveen . | |
| 4,388,747 | 6/1983 | Plummer . | |
| 4,449,531 | 5/1984 | Cerwin et al. . | |
| 4,514,885 | 5/1985 | Delahousse et al. . | |
| 4,586,503 | 5/1986 | Kirsch et al. . | |
| 4,887,601 | 12/1989 | Richards . | |
| 5,032,127 | 7/1991 | Frazee et al. . | |
| 5,222,961 | 6/1993 | Nakao et al. . | |
| 5,236,440 | 8/1993 | Hlavacek . | |
| 5,452,500 | 9/1995 | Revis . | |
| 5,464,413 | 11/1995 | Siska, Jr. et al. . | |
| 5,625,931 | 5/1997 | Visser et al. . | |

FOREIGN PATENT DOCUMENTS

| | | |
|---|---|---|
| 1 149 106 | 7/1983 | (CA) . |
| 30 14 578 | 11/1981 | (DE) . |
| 34 04 561 | 8/1984 | (DE) . |
| 34 43 367 | 6/1985 | (DE) . |

* cited by examiner

Primary Examiner—Cary E. O'Connor
(74) Attorney, Agent, or Firm—Barry R. Lipsitz

(57) ABSTRACT

In the case of a U-shaped surgical clip having two arms that are connected to one another via a deformable web, in order to stabilise the inherently deformable web in the non-deformed state it is proposed that the web bears, at least in some sections, a parallel web which is fixed on either side of the web and which restricts the deformability of the web in the reinforcing section of the web in which the parallel web and web are disposed next to one another.

17 Claims, 5 Drawing Sheets

SURGICAL CLIP

The present invention relates to the subject matter disclosed in German patent application 198 58 581.0 of Dec. 18, 1998, the entire specification of which is incorporated herein by reference.

BACKGROUND OF THE INVENTION

The invention relates to a U-shaped surgical clip having two arms that are connected to one another via a deformable web.

With such surgical clips the application is performed by compressing the two arms, whereby the vessel to be clamped is disposed between the arms. The web connecting the two arms has to be deformed at the same time, i.e. it is distorted, and in so doing it is desirable to require the smallest possible deformation forces for the distortion of the web during the application operation. On the other hand, the web however has to have a certain stability in the non-deformed state of the clip, since it has to be ensured that the clip remains in the open state, for example upon insertion into an application magazine. In such magazines the clips are guided by laying the outer side of the arms against guide faces, and it is therefore important that the spacing of the arms is maintained; the web is responsible for ensuring this spacing and it therefore has to apply a certain strength.

SUMMARY OF THE INVENTION

The object of the invention is to construct a generic surgical clip so that it firstly has sufficient stability in the web region at least in the non-deformed state, but upon deformation offers slight resistance in this region.

This object is achieved in accordance with the invention with a surgical clip of the type described at the beginning in that the web at least in some sections bears a parallel web that is fixed to either side of the web, and which restricts the deformability of the web in the reinforcing section of the web in which the parallel web and web are disposed next to one another.

Such a reinforcement of the web, which occurs at least in some sections, results in that the non-deformed web can keep the arms spaced from one another in the desired manner, secondly upon the deformation of the web, possibly with the simultaneous deformation of the parallel web, it is possible to reduce this strength, since curved webs can offer slight resistance to such a deformation by virtue of the geometric changes.

It is particularly advantageous if the strength of the parallel web is less than that of the web, so that the parallel web breaks upon the deformation of the web and consequently the reinforcement in the reinforcement section is removed.

It may be particularly specified that the reinforcing section is the central section of the web.

In a preferred embodiment it is specified that the web is bulged in a curve in the reinforcing section and the parallel web is disposed on the inner side of the bulge.

In particular with such an arrangement it is favorable if the parallel web bears projections which upon the bending aside of the web in the reinforcing section lie against the web and as a result maintain the bulge. As a result the bulged web is prevented from being deformed upon the distortion of the web with the formation of impermissibly small curvatures, which could result in damage.

In particular, the projections may be thickened portions in the parallel web, between which a weakened predetermined breaking point of the parallel web is situated. Thus it is possible that, even after the breaking of the parallel web, the thickened portions still guarantee the bulging of the web in the reinforcing section.

The parallel web can join the web with both ends, in a modified embodiment it may also be specified that the parallel web extends between two projections of the web, for example when the web bears catch projections which, when the clip is applied, engage in catch recesses of the arms. In another embodiment it is specified that the parallel web extends between a projection of the web on the one hand and the web itself on the other hand.

It is advantageous if the web is constructed as a flexible strip, at least in the reinforcing section, so that an integral hinge connection is constructed.

In a preferred embodiment it is also specified that, via the junction point of the arms with the web, the arms comprise rearwardly projecting extensions which bear catch means, which upon the compression of the arms fix the extensions to one another. As a result it is ensured that the deformed clip remains in the compressed position even when the web itself has not got a sufficiently stable construction to absorb the entire clamping forces of the clip.

At the same time it is advantageous if the catch means fixing the extensions to one another are disposed at the rear end of the extensions.

Furthermore, it may be specified that at the front end of the clip the arms bear catch means, which fix the arms to one another upon the compression of the arms. These catch means also hold the two arms together in the applied state, these catch means can be provided either alone or in combination with the catch means on the rear end of the arms.

The clip is preferably made from plastics material, in particular from a reabsorbable plastics material.

It is favorable if both arms are outwardly curved and the convex sides are faced towards one another, and as a result the central regions of the applied clip exert uniform compressive forces on the clamped container.

This effect is further enhanced if the arms have a smaller cross section in the central region than in the front region and than in the rear region.

The following description of preferred embodiments of the invention serves for further explanation in conjunction with the drawings.

DETAILED DESCRIPTION OF THE INVENTION

Figure 1:
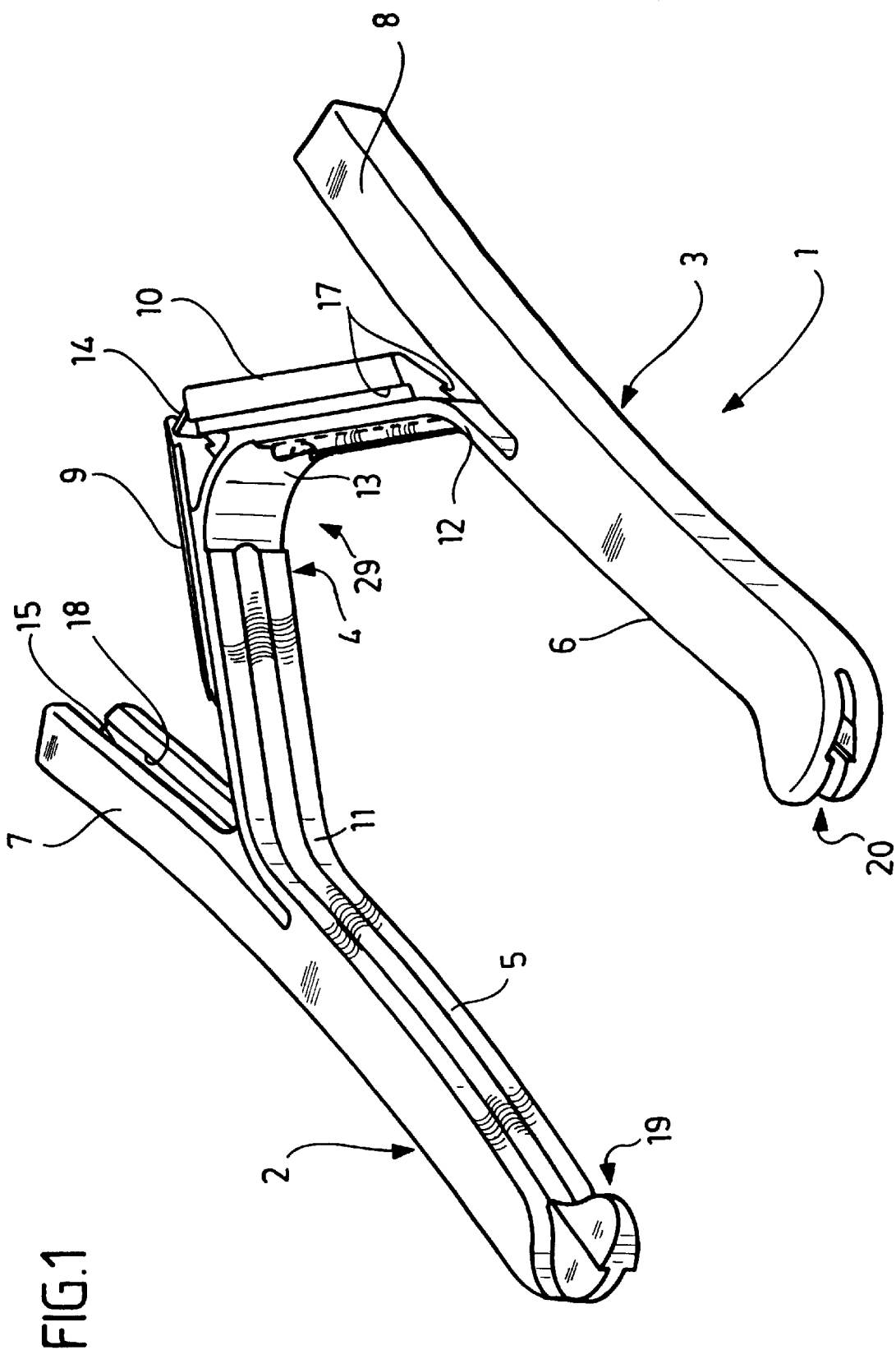
FIG. 1 shows a perspective view of a surgical clip in the non-deformed state.
Figure 2:
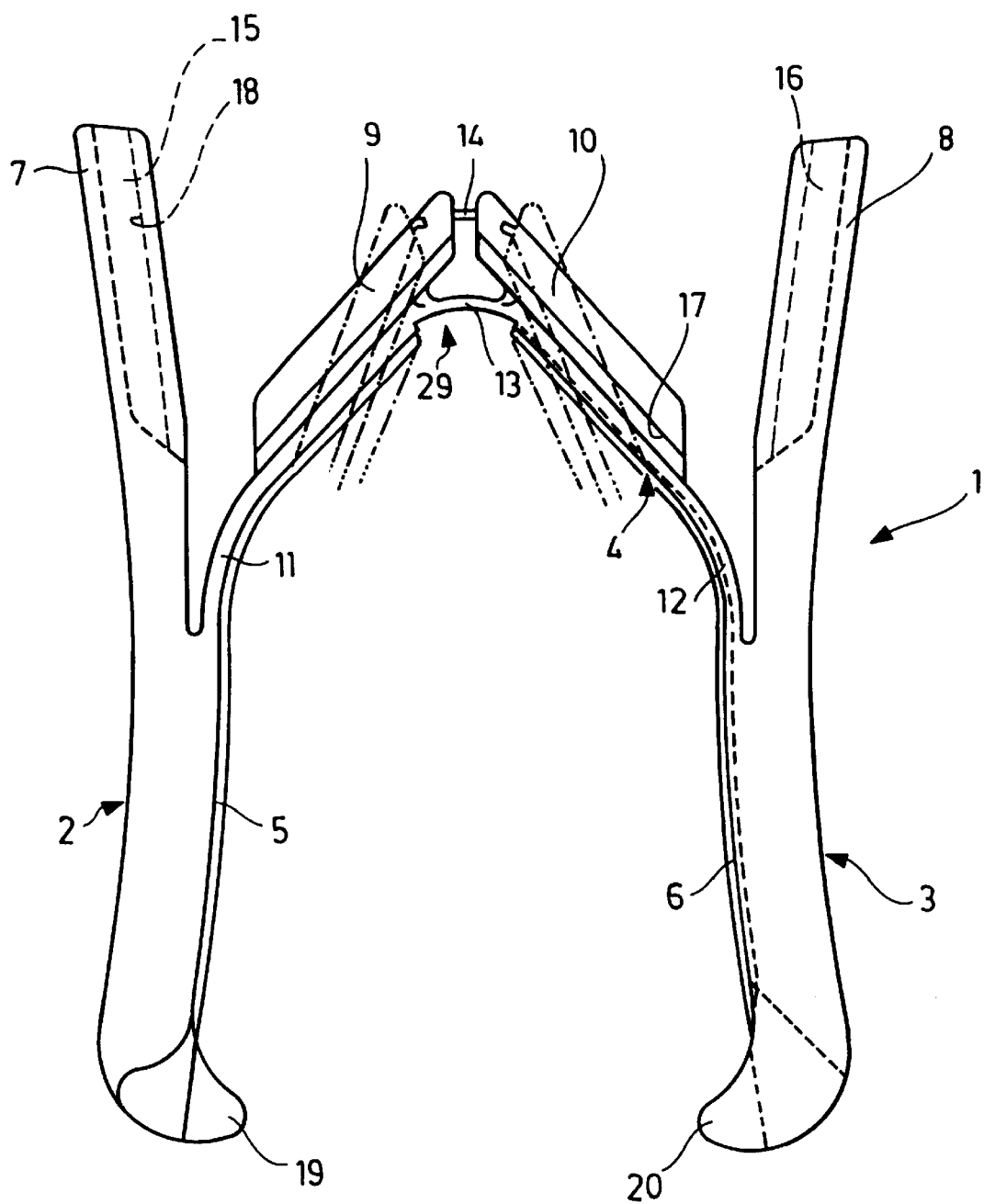
FIG. 2 shows a top view of the surgical clip of FIG. 1 in the non-deformed state (unbroken lines) and in the deformed state (dash-dot lines)

The clip 1 represented in FIGS. 1 and 2 comprises two arms 2, 3 that extend substantially parallel to one another and have a substantially rectilinear construction with a slight outward curvature, so that the convex inner sides of these arms 2 and 3 are faced towards one another.

In the central region both arms 2, 3 comprise a cross section which is reduced in relation to the front and the rear end, and in this central region both arms 2, 3 are connected to one another via a strip-shaped flexible web 4.

The inner sides of the two arms 2, 3 form clamping jaws 5, 6 between the front end and the junction of the web 4, which may be contoured in a suitable manner known per se, and the portion of the arms 2, 3 between the rear end and the junction of the webs 4 forms an extension 7, 8 in each case.

The web 4 bears on its outer side, spaced from one another and symmetrically to its centre, two ledge-shaped projections 9, 10, which strengthen the web 4 over its length and in this manner define three hinge-joint regions, namely a hinge-joint region 11 at the junction of the web 4 into the arm 2, a hinge-joint region 12 at the junction of the web 4 into the arm 3 and a central hinge-joint region 13 between the two projections 9 and 10.

The two projections 9 and 10 are connected to one another via a parallel web 14, which extends parallel to the central hinge joint region 13 spaced from the web 4 and which stabilises the web 4 in the central hinge-joint region 13, so that the two projections 9 and 10 and the portions of the web 4 associated therewith enclose a fixed angle with one another, for example an angle of roughly 90°, when the clip is not deformed. The strength of the parallel web 14 is chosen so that upon the bending together of the web by the deformation of the central hinge-joint region 13, the parallel web 14 breaks open and thus easily permits a deformation of the central hinge-joint region 13.

Situated in the two extensions 7 and 8 are longitudinal grooves 15, 16 that are open to the inside and which are disposed and dimensioned so that, upon the compression of the two arms 2 and 3 and the resultant folding together of the sections of the web 4, the projections 9 and 10 dip into the longitudinal grooves 15 and 16. In this inserted position the projections 9 and 10 are retained in the longitudinal grooves 15 and 16 are either frictionally by clamping or by positive locking, in the represented exemplified embodiment the projections 9 and 10 comprise lateral catch projections 17, which engage behind corresponding catch projections 18 in the longitudinal groves 15, 16. The catch projections 17 and 18 are elastically deformable, so that upon the entry of the projections 9 and 10 into the longitudinal grooves 15 and 16 they yield and enable the entry, but the projections 9 and 10 are prevented from moving out of the longitudinal grooves 15 and 16 by the catch projections 17 and 18.

The clip represented in FIGS. 1 and 2 is made from plastics material, in particular from a reabsorbable plastics material, and is preferably constructed as a single-part component.

To apply this clip, said clip is for example displaced in a magazine by the arms 2 and 3 abutting guides with their outer sides. This position is stabilised by the central hinge-joint region 13 of the web 4 being firstly strengthened by the parallel web 14, so that a reinforcing section 29 is produced, as a result of which a perfect guidance in the magazine is guaranteed without the danger of jamming.

For the application itself, the arms 2 and 3 of the opened clip 1 are moved up to a vessel (e.g., blood vessel) to be clamped, and then the two arms 2 and 3 are guided towards one another by a suitable tool, so that the clamping jaws 5 and 6 clamp the vessel enclosed between them in the desired manner.

In so doing the parallel web 14 breaks open, the web 4 is deformed until the web sections lie against the inner side of the extensions 7 and 8, and in this position the web is stabilised by the dipping of the projections 9 and 10 into the longitudinal grooves 15 and 16, i.e. in the rear part of the clip it is no longer possible to distance the arms 2 and 3 from one another.

Projections 19, 20 that are directed towards one another and that are constructed as catch projections are represented in the front region in the exemplified embodiment of FIGS. 1 and 2, so that when the arms 2 and 3 are brought closer to one another they are also locked with one another in the front region, with the result that there too it is no longer possible to distance the arms 2 and 3 from one another.

Figure 3:
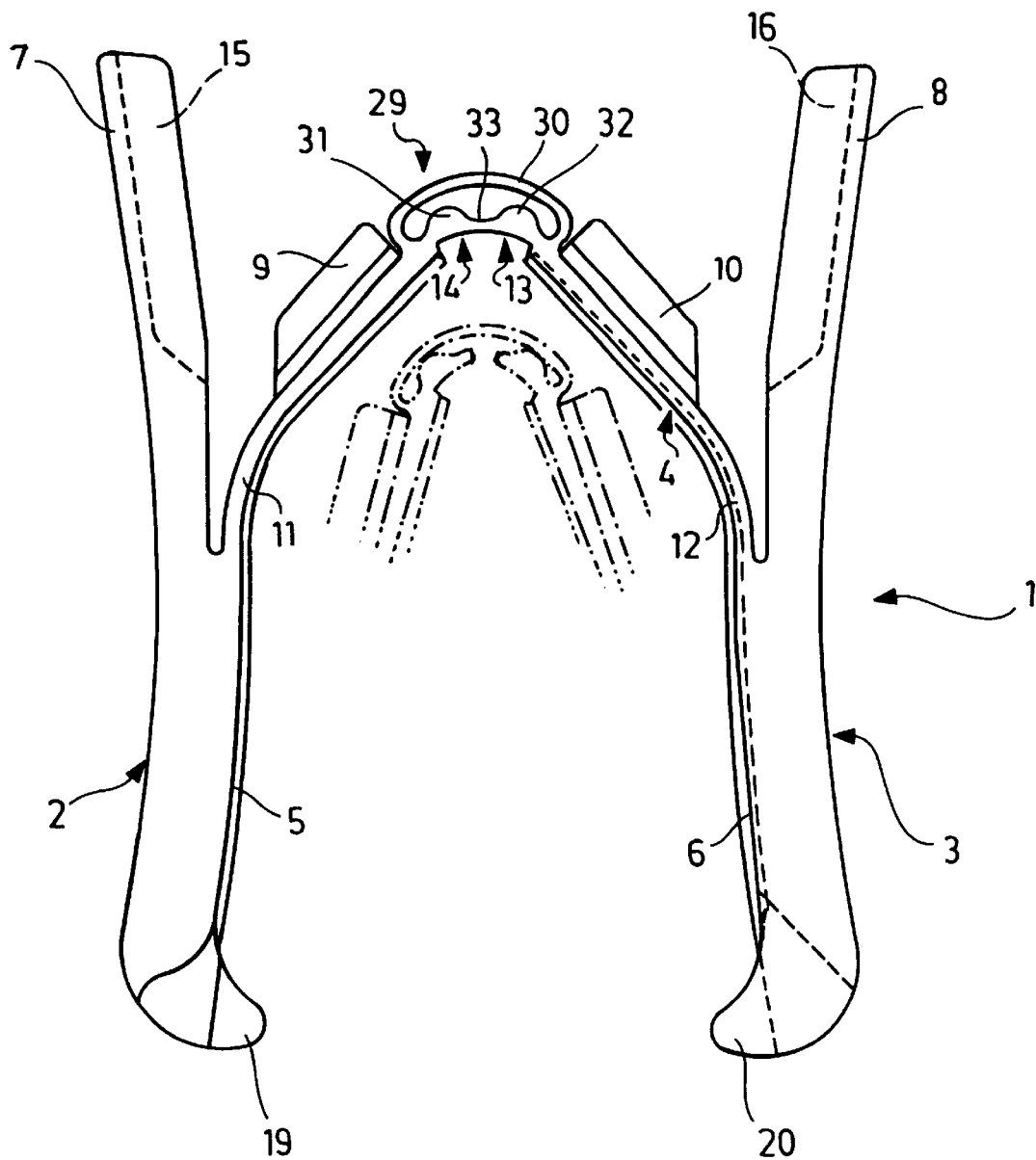
FIG. 3 shows a view similar to FIG. 2 of another preferred exemplified embodiment of a surgical clip.

Represented in FIG. 3 is a clip which corresponds to that of FIGS. 1 and 2 to a large extent, and parts that correspond with one another therefore bear the same reference numbers.

In contrast to the clip in FIGS. 1 and 2, here the parallel web 14 is not disposed between projections 9 and 10, but the web 4 itself forms in the central hinge-joint region 13 between adjacent projections 9 and 10 a portion 30 that is outwardly bulged in a curve, while on the inner side of this outwardly bulged portion 30 the parallel web 14 merges into the web 4. The parallel web 14 comprises two thickened portions 31, 32 over its longitudinal extension, which project towards the bulged portion 30 of the web 4 and which between them enclose a weakened predetermined breaking point 33.

In the case of the non-deformed clip (FIG. 3 in unbroken lines) the portion 30 of the web 4 is strengthened by the parallel web 14 with the formation of a reinforcing section 29, however upon the compression of the arms 2 and 3 the parallel web 14 breaks open in the region of the predetermined breaking point 33 and with the thickened portions 31 and 32 is applied from the inside against the portion 30 that bulges in a curve. As a result the web is slightly deformable in the central hinge-joint region 13, the thickened portions 31 and 32 guarantee that the portion that bulges in a curve 30 retains its bulge and is not extended with the formation of regions of very small curvature and thus is not possibly damaged.

Figure 4:
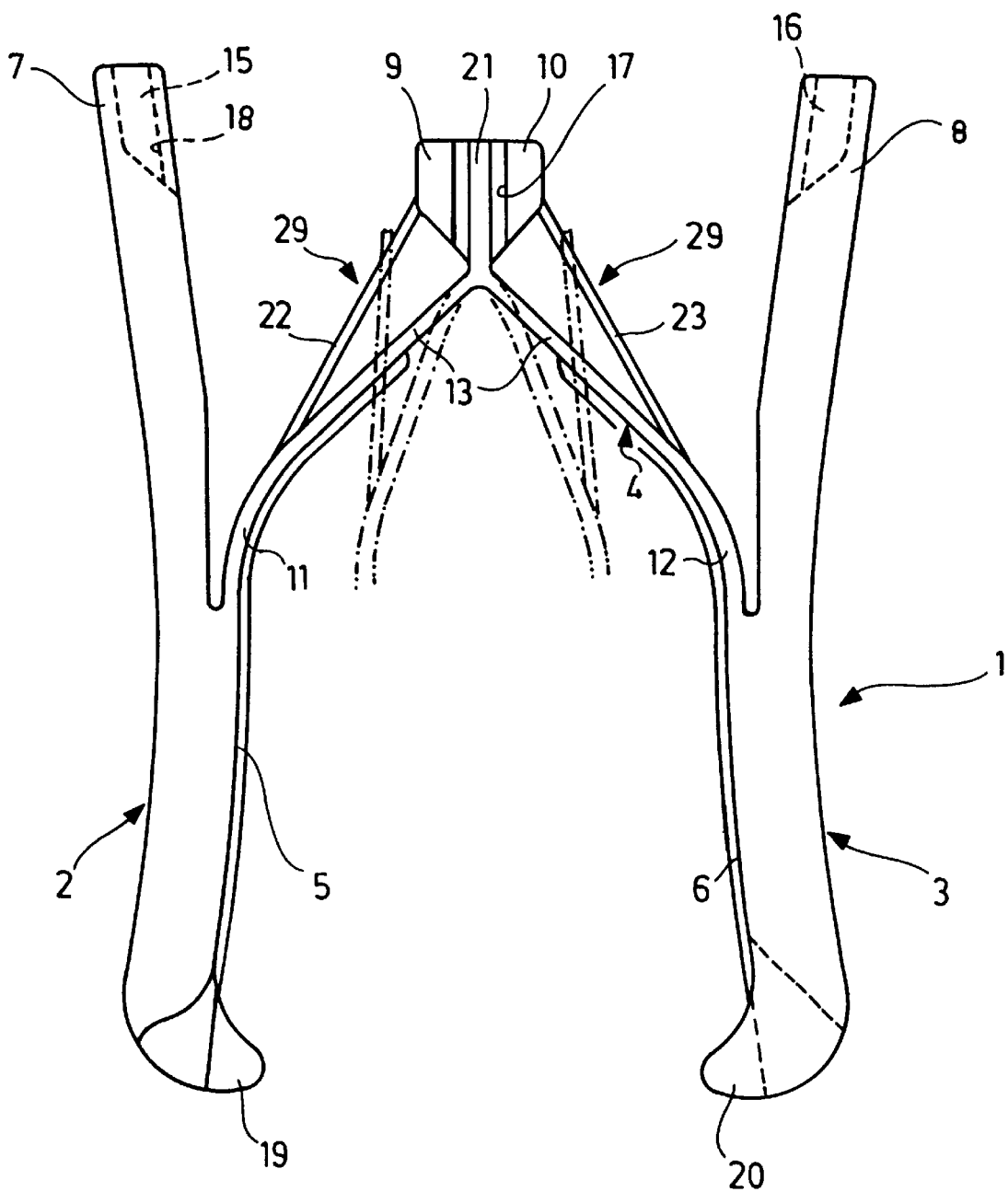
FIG. 4 shows a view similar to FIG. 2 of another preferred exemplified embodiment of a surgical clip and FIG. 5 shows a view similar to FIG. 1 of a clip represented in a simplified manner with catch means for connecting the two arms at the rear end.

Represented in FIG. 4 is a modified exemplified embodiment of a clip, which has a very similar design to the clip in FIG. 1, and identical parts therefore bear the same reference numbers.

In contrast to the clip in FIGS. 1 and 2, projections 9 and 10 in this exemplified embodiment are not placed directly on the outside of the web 4, but these projections 9 and 10 are integrally formed on a lateral lug 21, which in the centre of the web 4 protrudes from said web. All remaining regions of the web 4 are constructed as flexible strip material, however these regions are stabilised with the formation of a reinforcing section 29 by parallel webs 22 and 23, which connect the projections 9 and 10 each with a part of the web 4 that is remotely situated. Here too the parallel webs 22 and 23 have a weaker construction than the web 4 itself, so that upon the compression of the clip the parallel webs 22 and 23 break open and enable a free deformation of the web 4.

As in the exemplified embodiment of FIGS. 1 and 2, the projections 9 and 10 dip into the longitudinal grooves 15 and 16 when the clip is compressed.

Figure 5:
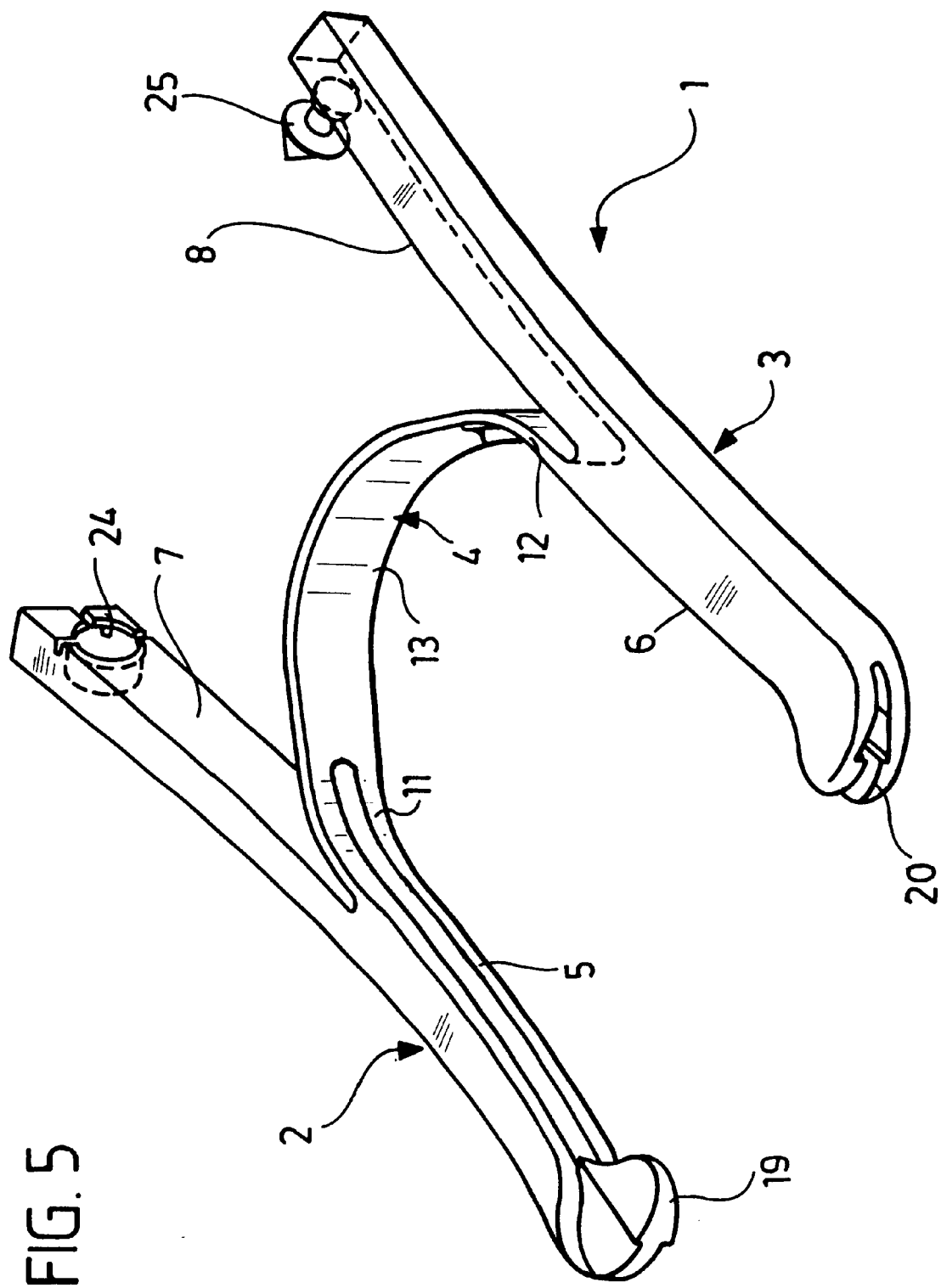

Finally, the clip represented in FIG. 5 is restricted in its representation to the two arms 2 and 3 and the web 4, however it is obvious that with this clip too the remaining configurations of the exemplified embodiments described can be used.

In addition to the catch means already described, in this exemplified embodiment interacting catch projections 24 and catch recesses 25 are also provided at the rear end of the arms 2 and 3, i.e. at the rear end of the extensions 7 and 8, and when the clip is compressed said projections and recesses directly fix the arms 2 and 3 to one another also at the rear end. Such a locking combined with the locking of the web 4 with the extensions 7 and 8 and combined with the locking of the projections 19 and 20 produces a clip which in the applied state clamps an enclosed container in a permanent and strong manner without there being the danger of this clip unintentionally opening.

In this case the retaining forces are not produced by bending resistance of the web 4, so that the web 4 itself can have a flexible and easily deformable construction, with the result that the application of the clip 1 is facilitated.

What is claimed:

1. A U-shaped surgical clip having two arms that are connected to one another via a deformable web, wherein:
    the web bears, at least in some sections, a parallel web that is fixed to either side of the web and that restricts the deformability of the web in a reinforcing section of the web in which the parallel web and web are disposed next to one another;
    the web is bulged in a curve in the reinforcing section and the parallel web is disposed on the inside of the bulge, and
    the parallel web bears projections which upon the bending aside of the web in the reinforcing section lie against the web and as a result maintain the bulge.

2. The surgical clip of claim 1, wherein the strength of the parallel web is less than that of the web.

3. The surgical clip of claim 1, wherein the reinforcing section is the central portion of the web.

4. The surgical clip of claim 1, wherein the projections are thickened portions in the parallel web between which a weakened predetermined breaking point of the parallel web is situated.

5. The surgical clip of claim 1, wherein the parallel web extends between two projections of the web.

6. The surgical clip of claim 1, wherein the parallel web extends between a projection of the web on the one hand and the web itself on the other hand.

7. The surgical clip of claim 1, wherein the web is constructed as a flexible strip at least in the reinforcing section.

8. The surgical clip of claim 1, wherein the arms, via the junction point of the arms with the web, comprise rearwardly projecting extensions which carry catch means, which upon pressing together of the arms fix the extensions to one another.

9. The surgical clip of claim 8, wherein the catch means fixing the extensions to one another are disposed at the rear end of the extensions.

10. The surgical clip of claim 1, wherein the arms, via a junction point of the arms with the web, comprise rearwardly projecting extensions which carry catch means, which upon pressing together of the arms fix the extensions to one another.

11. The surgical clip of claim 10, wherein the catch means fixing the extensions to one another are disposed at the rear end of the extensions.

12. The surgical clip of claim 1, wherein the arms bear catch means at the front end of the clip, which fix the arms to one another upon pressing together of the arms.

13. The surgical clip of claim 1, wherein the arms bear catch means at a front end of the clip, which fix the arms to one another upon pressing together of the arms.

14. The surgical clip of claim 1, being made from plastics material.

15. The surgical clip of claim 14, wherein the plastics material is reabsorbable.

16. The surgical clip of claim 1, wherein both arms are outwardly curved and the convex sides are faced towards one another.

17. The surgical clip of claim 1, wherein the arms have a smaller cross section in the central region than in the front region and than in the rear region.

* * * * *